United States Patent

Ayer et al.

[11] Patent Number: 5,840,074
[45] Date of Patent: *Nov. 24, 1998

[54] METHOD AND APPARATUS FOR DELIVERING FIRST AGENT FOLLOWED BY SECOND AGENT

[75] Inventors: Atul Devdatt Ayer, Palo Alto; James B. Eckenhoff; Jeremy C. Wright, both of Los Altos; Anthony L. Kuczynski, Palo Alto, all of Calif.

[73] Assignee: ALZA Corporation, Palo Alto, Calif.

[ * ] Notice: The portion of the term of this patent subsequent to Sep. 3, 2008, has been disclaimed.

[21] Appl. No.: 852,248

[22] PCT Filed: Dec. 21, 1990

[86] PCT No.: PCT/US90/07598

§ 371 Date: Jun. 2, 1992

§ 102(e) Date: Jun. 2, 1992

[87] PCT Pub. No.: WO91/10423

PCT Pub. Date: Jul. 10, 1991

Related U.S. Application Data

[63] Continuation-in-part of Ser. No. 463,109, Jan. 10, 1990, Pat. No. 5,045,082.

[51] Int. Cl.⁶ ..................................................... A61K 9/22
[52] U.S. Cl. ................................. 604/892.1; 604/890.1; 424/438; 424/457; 424/468
[58] Field of Search ............................. 604/890.1, 891.1, 604/892.1, 49.54, 56; 424/438, 422, 464, 468, 423–426, 471, 473, 451, 457; 128/898

[56] References Cited

U.S. PATENT DOCUMENTS

| | | | |
|---|---|---|---|
| 3,995,632 | 12/1976 | Nakano et al. . | |
| 4,381,780 | 5/1983 | Holloway | 604/892.1 |
| 4,449,983 | 5/1984 | Cortese et al. | 604/892.1 |
| 4,564,363 | 1/1986 | Bagnall et al. | 604/891.1 |
| 4,576,604 | 3/1986 | Guittard et al. | 604/890.1 |
| 4,578,263 | 3/1986 | Whitehead | 424/15 |
| 4,595,583 | 6/1986 | Eckenhoff et al. | 424/15 |
| 4,608,048 | 8/1986 | Cortese et al. | 604/890.1 |
| 4,612,186 | 9/1986 | Eckenhoff et al. | 424/15 |
| 4,643,731 | 2/1987 | Eckenhoff | 604/892.1 |

(List continued on next page.)

FOREIGN PATENT DOCUMENTS

| | | |
|---|---|---|
| 0226884 | 7/1987 | European Pat. Off. . |
| 0321043 | 6/1989 | European Pat. Off. . |
| 0325492 | 7/1989 | European Pat. Off. . |
| 1372040 | 10/1974 | United Kingdom . |
| 8600519 | 1/1986 | WIPO . |

*Primary Examiner*—Ronald K. Stright, Jr.
*Attorney, Agent, or Firm*—Paul L. Sabatine; Pauline A. Clarke; Christopher P. Rogers

[57] ABSTRACT

The invention provides a dispensing device (10) comprising a loading dose (32) (first agent delivery device) for short-term and continuous delivery of agent, retained together with a long-term dispensing device (12) (second agent delivery device) capable of long-term and continuous delivery of agent. The combination of first and second agent delivery device provides a device in which a substantially constant dose of beneficial agent is delivered to the environment of use over time. A rapid delivery of beneficial agent is followed by continuous and prolonged delivery of agent. In a preferred embodiment the device includes (A) a loading dose chamber (30) and retaining device (16) retaining a loading dose (32) (short-term delivery device) for rapid and continuous delivery of agent to the environment of use; and (B) a long-term dispensing device (12) (long-term delivery device) comprising a semipermeable wall (14) which surrounds and defines an internal lumen (20), a driving source (22) (expansion device) in the lumen for expanding and occupying an increased volume of the lumen, a beneficial agent (24) in the lumen that provides a dispensable formulation to the environment of use, and an exit (28) in the device for delivery of the beneficial agent to the environment of use over time. A densifier (26) and/or a moveable barrier device (34) may also be included in the lumen of the long-term dispensing device.

23 Claims, 2 Drawing Sheets

U.S. PATENT DOCUMENTS

| | | | |
|---|---|---|---|
| 4,662,880 | 5/1987 | Hamel et al. | 604/892.1 |
| 4,704,118 | 11/1987 | Eckenhoff | 604/892 |
| 4,729,793 | 3/1988 | Eckenhoff et al. | |
| 4,772,474 | 9/1988 | Eckenhoff et al. | 424/465 |
| 4,810,502 | 3/1989 | Ayer et al. | 424/473 |
| 4,842,867 | 6/1989 | Ayer et al. | 424/473 |
| 4,915,952 | 4/1990 | Ayer et al. | 424/467 |
| 4,915,953 | 4/1990 | Jordan et al. | 424/473 |
| 4,915,954 | 4/1990 | Ayer et al. | 424/473 |
| 4,927,419 | 5/1990 | Scully | 604/892.1 |
| 5,045,082 | 9/1991 | Ayer et al. | 604/892.1 |

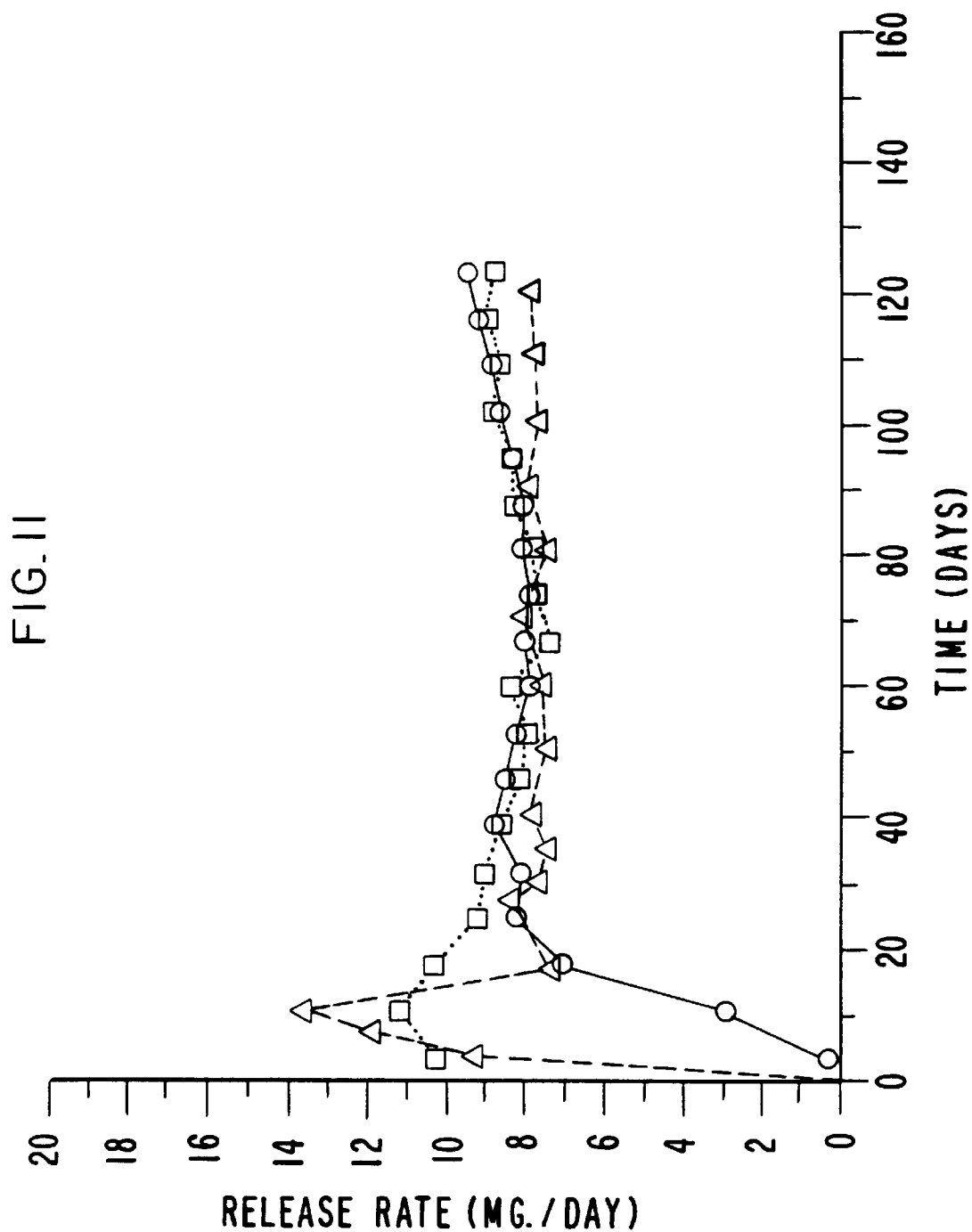

METHOD AND APPARATUS FOR DELIVERING FIRST AGENT FOLLOWED BY SECOND AGENT

This application is a continuation-in-part of U.S. application Ser. No. 07/463,109, filed Jan. 10, 1990, now U.S. Pat. No. 5,045,082.

FIELD OF THE INVENTION

This invention pertains to the provision of a loading dose in long-term agent delivery devices. More particularly, the invention relates to the provision of a beneficial agent loading dose as a part of a long-term beneficial agent delivery device having a semipermeable wall and a reservoir containing a beneficial agent formulation, an expansion means, and, optionally, a density means. Such delivery devices find use in medical and veterinary delivery of medication and nutrients to humans and animals over a prolonged period of time.

BACKGROUND OF THE INVENTION

Agent delivery systems and devices which use an expansion means can deliver a beneficial agent to an environment of use over a period of hours, days, or months. The expansion means absorbs liquid, expands, and acts to drive out beneficial agent formulation from the interior vice in a controlled manner.

Agent delivery devices which use an expansion means can be designed to deliver agent over a relatively short term, i.e., 20–25 days or less. Such devices generally comprise a highly permeable semipermeable membrane, together with a beneficial agent in a carrier which is liquid, relatively non-viscous, and easily extruded by the action of the expansion means. The agent delivery profile of such a short-term device is shown, for example, in FIG. 12 of U.S. Pat. No. 4,595,583, the disclosure of which is hereby incorporated by reference. As shown in U.S. Pat. No. 4,643,731, the disclosure of which is hereby incorporated by reference, instantaneous concentration of beneficial agent obtained from short-term devices can be achieved by providing a loading dose, i.e., an initial, immediate, short-term dose of beneficial agent, prior to the onset of the continuous delivery provided by the osmotic pump device.

Agent delivery devices can alternatively be designed to deliver agent over a longer term, i.e., 25–30 days or greater, and especially 60–120 days or greater. Such devices generally comprise a slowly permeable semipermeable membrane, together with a beneficial agent in a carrier which is viscous or paste-like and extruded by the action of the expansion means over relatively longer times than shown by the short-term devices. The startup time of the device, that is, the time during which the device does not deliver beneficial agent, depends upon the rate at which the semipermeable membrane allows hydration of the system and the rate at which the expansion means becomes hydrated sufficiently to begin extrusion of the beneficial formulation. The agent delivery curve of a device designed to deliver a given dosage for 120 days is shown, for example, in FIG. 21 of U.S. Pat. No. 4,729,793.

The teachings of the prior art pertaining to loading doses of beneficial agent regarding short-term delivery devices do not provide a solution to the problem of the startup delay in long-term devices. Due to the kinetics of the release of loading doses for short-term devices, the loading doses are active for only a short time and do not sustain the concentration of beneficial agent during the startup period demonstrated by long-term devices. Those loading doses provided within the coating of a short-term device are not appropriate for use with long-term devices having a semipermeable membrane, as such coatings can interfere with the permeability of the semipermeable membrane, and thus interfere with the operation of the device.

Ruminant animals, including cattle, sheep, goats, deer, bison, camels and giraffes, and especially domestic animals such as cattle, sheep and goats, comprise an important group of animals that require periodic administration of medicines and nutrients. The medicines and nutrients are administered for the treatment and alleviation of various conditions and for improved health. Ruminants have a complex stomach generally having three or four compartments. The largest of the stomach compartments is the rumen, which acts as an important location for receiving and passing medicines and nutrients into other compartments, including the abomasum and the intestine.

One method of treating ruminants requires the repeated administration of medicines and nutrients at frequent time intervals. This form of treatment is inconvenient and expensive and does not lend itself to reliable therapy.

Prior art devices which have been designed to maintain continuous dosages of a beneficial agent for extended periods of time have the disadvantage of exhibiting a significant startup time between administration to the subject animal or human and the onset of agent delivery. Provision of effective dosages upon administration of the device has been obtained by prehydration (i.e., soaking) of the device prior to administration. For example, a prior art device which exhibits a three-week delay prior to onset of effective delivery of the desired agent can be soaked for three weeks prior to administration to the subject. Effective delivery of the desired agent thus begins upon administration.

Prehydration of a long-term device has several significant disadvantages. The soaking of a single device for a period of three weeks requires a processing step which is undesirable but which is likely to be manageable. The soaking of sufficient individual devices with which to supply an entire herd of animals can require a container the size of a swimming pool or a small lake. The active agent which is being delivered by the device is distributed into the water in which the device is soaked, and can require special treatment of the water before it can be released into ground or sewage waters. Additionally, if the device has a limited lifespan (i.e., decomposition of the semipermeable membrane, density means, or other component of the device takes place over time), the time during which the device is prehydrated may limit the effective use in the subject animal.

It is therefore an object of this invention to provide a long-term dispensing device that quickly and continuously delivers an effective amount of agent, followed by a continuous and sustained delivery of agent over a prolonged period of time.

Another object of the invention is to provide a long-term dispensing system comprising a first agent delivery means that quickly and continuously makes agent available, and a second agent delivery means that makes agent available for continuous and prolonged delivery, and thus provides a dispensing system that delivers agent quickly, continuously, and over a prolonged period of time when in operation in an environment of use.

Another object of the invention is to provide a first agent delivery means positioned within or at the surface of a long-term dispensing device comprising a second agent delivery means capable of long-term and continuous delivery of agent. The combination of first and second agent delivery means provides a device which exhibits beneficial agent rapidly delivered to the environment of use, together with continuous and prolonged delivery of agent, substantially eliminating the startup time associated with prior art devices.

Yet another object of the invention is to provide an improvement over the prior art by making available a dispensing device possessing controlled agent availability during a period of time during which the prior art dispensing devices did not make agent available to the environment of use.

Another object of the invention is to provide an improved beneficial agent dispensing device by providing a dispensing device which is easy to manufacture, inexpensive and easy to use, makes the desired agent quickly available, and provides constant and prolonged agent availability over time.

It is another object of the invention to provide a delivery device that can remain in the rumen of a ruminant for a prolonged period of time, providing both rapid and prolonged delivery of a beneficial agent.

These and other objects, features and advantages of the invention will be more apparent to those skilled in the art from the following specification, taken in conjunction with the drawings and the accompanying claims.

BRIEF DESCRIPTION OF THE INVENTION

The invention herein provides dispensing devices for delivering a beneficial agent formulation to an environment of use, together with methods of manufacture and use of such devices.

The subject invention comprises a loading dose (first agent delivery means) for rapid and continuous delivery of a first beneficial agent formulation to the environment of use, together with a long-term dispensing device (second agent delivery means) that provides continuous and prolonged delivery of a second beneficial agent formulation to the environment of use over time.

The loading dose provides a rapid and continuous delivery of a first beneficial agent formulation to the environment of use during the startup period of the long-term dispensing device. The loading dose is retained in contact with the long-term dispensing device during the startup period of the long-term dispensing device, and is exposed to the environment of use, releasing the beneficial agent formulation in a controlled manner. The amount of beneficial agent provided by the loading dose is designed to mesh closely with the delivery rate of beneficial agent provided by the long-term dispensing device so that delivery of the beneficial agent is as uninterrupted and continuous as possible.

The second agent delivery means provides continuous and prolonged delivery of a second beneficial agent formulation to the environment of use. The second agent delivery means comprises a semipermeable wall that surrounds and defines an internal lumen; an exit means in the dispensing device for delivery of the second beneficial agent formulation through the semipermeable wall to the environment of use; and a second beneficial agent formulation in the lumen that provides a dispensable formulation to the environment of use. An expansion means (driving source) is provided in the lumen to displace the second beneficial agent formulation from the interior of the lumen through the exit means to the environment of use. In one preferred embodiment, a density means is included in the lumen and acts to retain the dispensing device in the environment of use. In an especially preferred embodiment, the exit means comprises a passageway through the density means which is adapted to contain the first agent delivery means.

DESCRIPTION OF THE DRAWINGS

The drawings are not drawn to scale, but are set forth to illustrate various embodiments of the invention. Like numbers refer to like structures. The drawing figures are as follows:

FIG. 11 depicts the delivery curves of (a) a long-term delivery device which does not include a loading dose, and which has not been prehydrated (shown by circles); (b) a long-term delivery device which does not include a loading dose, and which has been subject to prehydration (shown by squares); and (c) a long-term delivery device of this invention, and which includes a loading dose (shown by triangles).

DETAILED DESCRIPTION OF THE INVENTION

Figure 1:
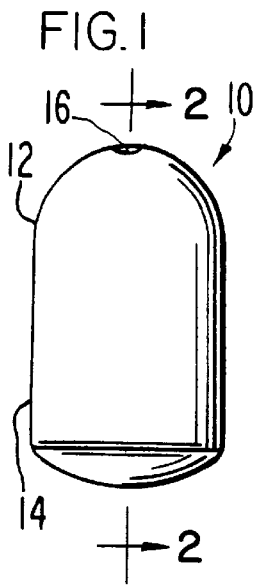
FIG. 1 is an external view of a delivery device designed and manufactured for administration of a beneficial agent to an animal.

The invention herein provides a device which is useful for delivering beneficial agent continuously to an environment of use over a prolonged period of time. The preferred environment of use comprises the rumen of a ruminant animal. However, the devices are not restricted to use in ruminant animals or to a rumen environment of use. Long-term dispensing devices of the invention find use, for example, in humans or other animals. The environment of use can comprise a body cavity such as the peritoneum, vagina, or intestinal tract. A single dispensing device or several dispensing devices can be administered to a subject during a therapeutic program.

The term "continuous" as used herein refers to delivery of a beneficial agent which, once begun, varies little with the passage of time for the life of the device. Generally, the delivery of beneficial agent will vary by less than 50%, preferably by less than 20%, and more preferably by less than 10% over the period of agent delivery. The "prolonged" delivery of agent refers to delivery of beneficial agent which continues for a period of 25 days or longer, generally 60 days or longer, and more generally for 120 days or longer.

The term "agent" as used herein describes any beneficial agent or compound that can be delivered by a device herein to produce a beneficial and useful result. The term beneficial agent includes medicines or drugs, such as inorganic or organic drugs, anthelmintics, antiparasitic agents such as avermectin and ivermectin, antimicrobial agents, antibiotics, sulfa drugs, antiflea agents, rumen fermentation manipulators and ionophores, minerals and mineral salts such as selenium, antibloat agents, growth supplements, hormones, steroids, estrus suppression agents such as melengestrol acetate, vitamins, antienteritis agents, nutritional supplements, and the like. It is to be understood that more than one beneficial agent may be incorporated into the beneficial agent formulation in a device of this invention, and that the use of the term "agent" in no way excludes the use of two or more such agents.

The first and second beneficial agent formulations need not contain the same beneficial agent. However, it is a preferred embodiment that the first and second beneficial agent formulations contain the same beneficial agent. The first and second beneficial agents can comprise the same biological agent provided in different or dissimilar forms, but preferably the effective dose of the forms is adjusted to provide constancy of dosage over time.

The first beneficial agent formulation, or loading dose, provides a dosage of beneficial agent to the environment of use substantially throughout the time prior to the consistent release of the second beneficial agent formulation from the device. The first beneficial agent formulation comprises at least one first beneficial agent homogeneously or heterogeneously dispersed or dissolved in an appropriate carrier means. The first beneficial agent can be provided in the controlled delivery form described in U.S. Pat. Nos. 3,845,770, 3,916,899, and 4,350,271, for example. Alternatively, the first beneficial agent can be incorporated into a solid, paste, gel, semisolid, or the like, or a thermosensitive material which provides a dispensable material in the environment of use. The first beneficial agent formulation can be provided in the form of a tablet or capsule, for example, and can be round, spheroid, toroid, cylindrical, square, and the like. Materials which can be added to the first beneficial agent to provide the first beneficial agent formulation include fillers such as avicels, polyethylene oxide, blends of polyethylene oxides of high and low molecular weight, sodium carboxymethyl cellulose, sodium carbomer, hydroxy propyl cellulose, and the like; binders such as polyvinyl povidone, hydroxypropyl methylcellulose, guar gum, alginates such as sodium alginate, and the like; osmotic agents such as sodium chloride, sorbitol, and the like; and disintegration agents such as starch, polyplasdone XL, and the like.

The release rate of a specific loading dose tableted formulation in which the hydrophobic beneficial agent is preferentially released by erosion can be approximated using the formula:

$$dm/dt = (K)(A/2)(Co)$$

wherein
dm/dt=dosage rate of delivery, mg/day
K=erosion constant
A=surface area exposed to erosion process
Co=drug loading of beneficial agent in formulation It can be seen that varying the exposed surface area, A, and/or drug loading, Co, will vary the release rate for a given first beneficial agent formulation.

The second beneficial agent formulation provides a long-term constant dosage of a dispensable formulation including at least one second beneficial agent. The second beneficial agent formulation is urged from the lumen to the environment of use by the action of the expansion means. In a preferred embodiment, the second beneficial agent is homogeneously or heterogeneously dispersed or dissolved in a thermoresponsive composition. Exemplary thermoresponsive compositions are detailed in U.S. Pat. No. 4,772,474, the disclosure of which is incorporated herein by reference.

In a preferred embodiment, the first beneficial agent formulation provides beneficial agent in a dosage curve to deliver a substantially constant dose of beneficial agent during the existence of the device. That is, the first beneficial agent formulation is designed to deliver less beneficial agent to the environment of use as the second beneficial agent formulation begins to deliver beneficial agent to the environment of use. For example, if the goal dosage of the long-term dispensing device is delivery of 8 mg/day of beneficial agent, the first beneficial agent formulation quickly and consistently delivers 8 mg/day of beneficial agent to the environment of use. As the second beneficial agent formulation begins delivery of beneficial agent at a rate of 1 mg/day, the rate of delivery of agent by the first beneficial agent formulation drops to 7 mg/day, for a total delivery of beneficial agent to the environment of use of 8 mg/day. Similarly, as the second beneficial agent formulation begins delivery of beneficial agent at a rate of 2 mg/day, the rate of delivery of agent by the first beneficial agent formulation drops to 6 mg/day, thus maintaining a total delivery to the environment of use of 8 mg/day. As the delivery rate of the second beneficial agent formulation approaches 8 mg/day, the first beneficial agent delivery means is depleted, and the delivery rate of the first beneficial agent formulation drops to 0 mg/day.

Referring now to the FIGURES:

FIG. 1 is an external view of a beneficial agent delivery device 10 designed and manufactured for administration of a beneficial agent to an animal, such as a ruminant animal. The delivery device 10 comprises a body 12 formed by a semipermeable wall 14 that surrounds and defines an internal lumen (not shown). The beneficial agent delivery device also comprises a passageway (not shown) which terminates at the semipermeable wall 14 and is covered by a retaining means 16.

Figure 2:
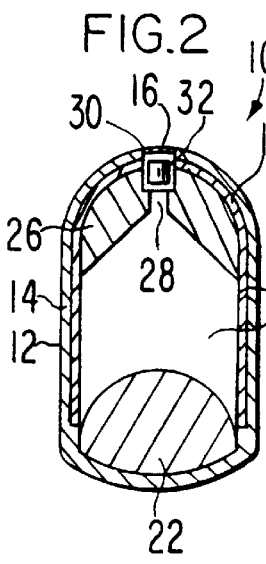
FIG. 2 is a cross-sectional view of the delivery device of FIG. 1 through 2—2 which illustrates the structure of the delivery device prior to or at the time of administration to an animal. Shown are a semipermeable outside wall, an internal capsule wall, a beneficial agent formulation, an expansion means, a density means, and a loading dose which is exposed to the environment of use.
Figure 3:
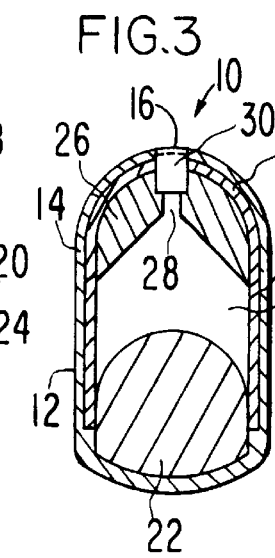
FIG. 3 is a view of the delivery device of FIG. 2 which illustrates the structure of the delivery device subsequent to administration of the device to an animal. The loading dose has been eroded by the environment of use, and expansion of the expansion means has commenced.
Figure 4:
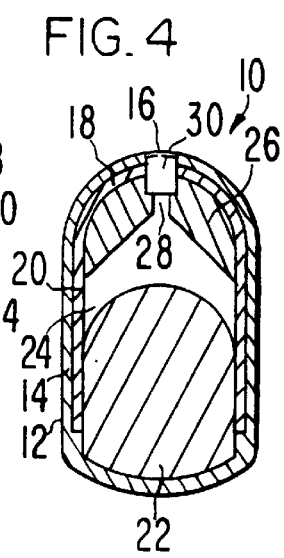
FIG. 4 is a view of the delivery device of FIG. 3 which illustrates the structure of the delivery device after continued use within the animal. The expansion of the expansion means has forced much of the beneficial agent formulation into the environment of use.

FIGS. 2–4 are cross-sectional views of the delivery device 10 of FIG. 1 through 2—2, and illustrates the structure of the delivery device 10 prior to and subsequent to the time of administration to an animal. The device comprises a body 12, defined by an external semipermeable wall 14. The semipermeable wall 14 surrounds an optional internal capsule wall 18, and surrounds and defines an internal compartment or lumen 20. The semipermeable wall 14 is formed of a semipermeable composition that is substantially permeable to the inward passage of fluid from the environment of use and is substantially impermeable to the outward passage of beneficial agent and other constituents found in the device. Materials which are appropriate for use in forming the semipermeable wall are known to the art and are set forth, for example, in U.S. Pat. No. 4,772,474, the disclosure of which has been incorporated by reference in its entirety.

The lumen 20 contains an expansion means 22 which acts to drive a second beneficial agent formulation 24 into the environment of use. Both the expansion means 22 and the second beneficial agent formulation 24 have a shape that corresponds to the internal shape of the lumen 20. The lumen 20 also contains a density means 26. The density means 26, also referred to as the densifier, is dense enough to retain the dispensing device in the environment of use. When the environment of use is the rumen of a ruminant, the density means is a necessary element of the dispensing device, and acts to retain the device in the rumen or reticular sac of the ruminant over a prolonged period of time. Appropriate density means are shown in U.S. Pat. Nos. 4,643,731 and 4,772,474, which have been incorporated by reference.

The expansion means 22 is positioned opposite the density means 26, with the second beneficial agent formulation 24 positioned between them. The expansion means 22, housed in the lumen 20 usually comprises a hydrogel composition which includes a swellable, expandable polymer and, optionally, an osmotically effective solute. The expansion means provides a driving source for delivering the second beneficial agent formulation 24 from the lumen 20 to the environment of use via the exit means 28. Materials which are appropriate for use in forming the expansion means are known to the art and are described in U.S. Pat. No. 4,772,474, for example, the disclosure of which has been incorporated by reference.

The density means 26 includes a passageway or exit means 28 which extends through the internal capsule wall 18 and the semipermeable wall 14 for metered delivery of the second beneficial agent formulation 24 to the environment of use. The exit means permits extrusion of second beneficial agent formulation from the lumen into the environment of use, and can be embodied by a passageway, aperture, bore, pore, and the like. Detailed descriptions of various passageways, the preferred maximum and minimum dimensions, and modes of manufacture are disclosed in U.S. Pat. Nos. 3,845,770 and 3,916,899, the disclosures of which are incorporated herein by reference in their entireties.

As shown in FIG. 2, the passageway also preferably includes a loading dose chamber 30, which, together with the retaining means 16, is designed to retain a loading dose 32, containing a formulation for the release of beneficial agent, in contact with the dispensing device 10 and in fluid contact with the environment of use. The retaining means 16, which covers the loading dose chamber, ensures that the first beneficial agent formulation is not separated from the long-term dispensing device or prematurely passed from the device. The retaining means 16 preferably intersects the exit means 28 at the surface of the device. The retaining means functions to keep the loading dose as an integral part of the dispensing device, but must also allow sufficient contact with the environment of use to permit consistent erosion of the loading dose over time. The retaining means can comprise, for example, a perforated plate, a screen, a porous membrane such as an open-pore or blown-pore membrane, a perforated membrane, and the like. The material must be physically and chemically stable in the environment of use.

In a preferred embodiment, the retaining means preferably also functions to provide back-pressure to the second beneficial agent formulation extrusion means. A sufficient amount of back-pressure should be present in the system to minimize the formation of gaseous materials within the second beneficial agent formulation and the passage of such gaseous materials into the environment of use.

Figure 5:
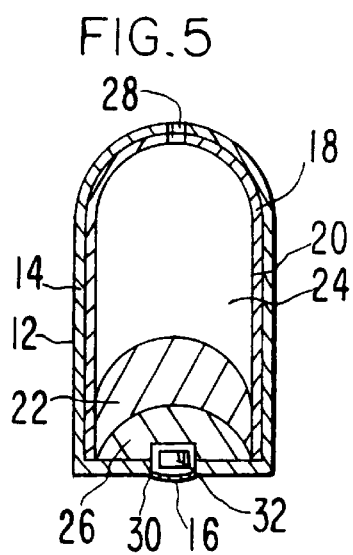
FIG. 5 is a view of a delivery device provided by the invention depicting an alternate internal structural configuration of elements comprising the delivery device.
Figure 6:
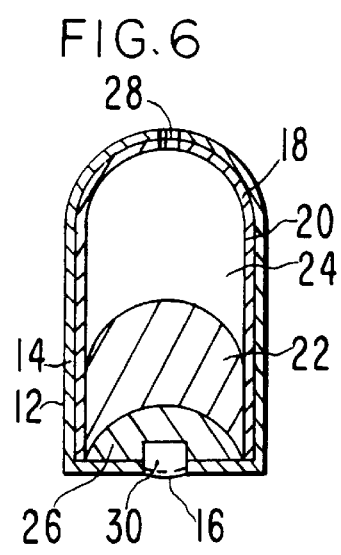
FIG. 6 is a view of the delivery device of FIG. 5 which illustrates the structure of the delivery device subsequent to administration of the device to an animal. The loading dose has been eroded by the environment of use, and expansion of the expansion means has commenced.
Figure 7:
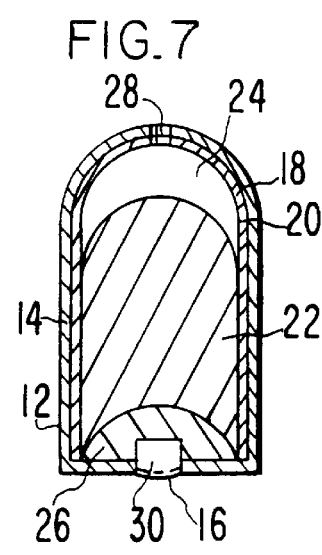
FIG. 7 is a view of the delivery device of FIG. 6 which illustrates the structure of the delivery device after continued use within the animal. The expansion of the expansion means has forced much of the beneficial agent formulation into the environment of use.

FIGS. 5–7 are cross-sectional views of a delivery device of the invention prior to and subsequent to administration to an animal. These drawings demonstrate an alternate internal structural configuration of elements comprising a delivery device. The density means 26 is located adjacent the expansion means 22, which in turn is located adjacent the second beneficial agent formulation 24. The passageway 28 comprises a bore or pore which extends through the internal capsule wall 18 and the semipermeable wall 14 for metered delivery of the second beneficial agent formulation 24 to the environment of use.

The loading dose compartment 30 is preferably integral to the exit means 28, but alternate configurations are possible. As shown in FIGS. 5–7, the loading dose compartment can be located at the surface of the device other than at the exit means. When the loading dose chamber is not integral to the exit means, it is preferably located adjacent to the density means, if a density means is present. In a less preferred configuration, the loading dose chamber is located adjacent the expansion means or adjacent the second beneficial agent formulation. Such positioning is generally less preferred, as the presence of the loading dose chamber or physical properties of the loading dose formulation can inhibit the flux of fluids through the semipermeable wall into the lumen. The loading dose chamber 30 and retaining means 16 maintain the loading dose 32 in contact with the dispensing device and in contact with the environment of use.

Figure 8:
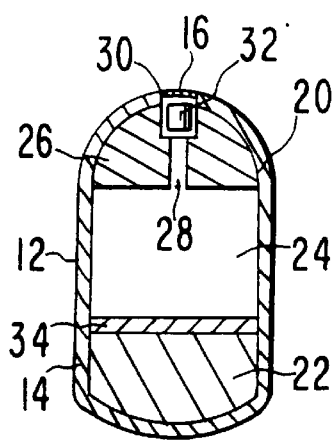
FIG. 8 is a view of a delivery device provided by the invention depicting an alternate internal structural configuration of elements comprising the delivery device. Shown are a semipermeable wall, a beneficial agent formulation, an expansion means, a means for optimizing delivery of the beneficial agent formulation, a density means, and a loading dose which is exposed to the environment of use.
Figure 9:
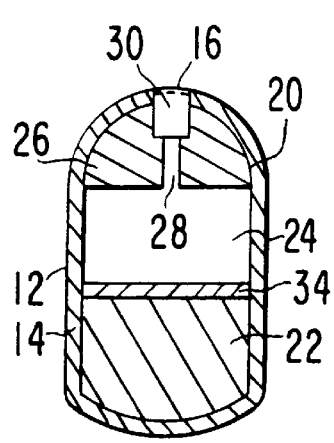
FIG. 9 is a view of the delivery device of FIG. 8 which illustrates the structure of the delivery device subsequent to administration of the device to an animal. The loading dose has been eroded by the environment of use, and expansion of the expansion means has commenced.
Figure 10:
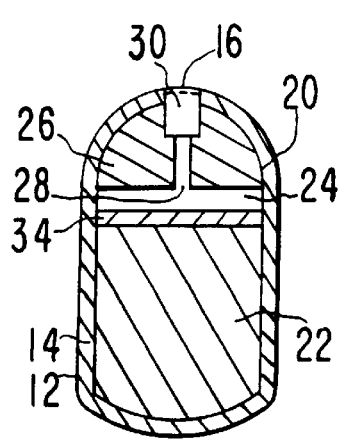
FIG. 10 is a view of the delivery device of FIG. 9 which illustrates the structure of the delivery device after continued use within the animal. The expansion of the expansion means has forced much of the beneficial agent formulation into the environment of use.

FIGS. 8–10 are cross-sectional views of a preferred embodiment of the delivery device of the invention prior to and subsequent to administration to an animal. The device comprises a body 12, defined by an external semipermeable wall 14. The semipermeable wall 14 surrounds an internal compartment or lumen 20. The lumen 20 contains an expansion means 22 and a second beneficial agent formulation 24, which are separated by a moveable barrier means 34. In a preferred embodiment of the delivery device herein, a moveable barrier means 34, or lamina, is present within the lumen 20 and maintains the separate identity of the second beneficial agent formulation 24 and the expansion means 22. Such an embodiment is further described in U.S. Pat. Nos. 4,772,474 and 4,844,984, the disclosures of which are incorporated herein in their entirety. The moveable barrier means conveys the expanding force of the expansion means 22 against the second beneficial agent formulation, to assist in the expulsion of beneficial agent from the lumen into the environment of use. Each of the expansion means 22, second beneficial agent formulation 24, and the moveable barrier means 34 has a shape that corresponds to the internal shape of the lumen 20.

The following examples are illustrative of the present invention. They are not to be construed as limitations of the scope of the invention. Variations and equivalents of these examples will be apparent to one skilled in the art in light of the present disclosure, the drawings, and the claims herein. All percentages are weight/weight percent, and all temperatures are in degrees Celsius, unless otherwise noted.

EXAMPLE 1

Manufacture of Dispensing Device without Loading Dose

Semipermeable wall: 50.5 Grams of cellulose acetate butyrate having a butyryl content of 17% and an acetyl content of 29% (Eastman), and 17.5 g cellulose acetate having an acetyl content of 39.8% (Eastman) were sized and combined with 22.0 g Citroflex-4™ (tributyl citrate, Morflex, Inc.), 6.0 g Citroflex-2™ (triethyl citrate, Pfizer, Inc.), and 4.0 g polyethylene glycol having a molecular weight of 400 (PEG 400, Union Carbide) in the bowl of a large mixer. After mixing for 20 minutes, the material was transferred to the feed hopper of an injector molder equipped with a suitable mold to produce a cellulosic cup weighing 10.1 g and having the following dimensions: 7.9 cm height, 2.5 cm width, and wall thickness of 0.17 cm.

Expansion means: A blend of 60.3 g sodium salt of polyacrylic acid having a MW of 3,000,000 (Sodium Carbomer™ 934P, B.F. Goodrich Chemical Co.), 0.9 g polyvinylpyrrolidone (PVP), 0.9 g magnesium stearate, 12.9 g water, and 25 g sodium chloride was made. 8.41 Grams of the blend was compressed under 9072 kg (10 tons) of force on a Stokes bolus tablet press to form compressed hydrophilic tablets which conform to the internal diameter of the cups described above. A compressed hydrophilic expansion member was inserted into the cup.

Moveable barrier means: 49 Grams of Multiwax™ 180M (Witco Chemical Co., Inc.), a food grade wax, was combined with 49 g Multiwax™ X145A (Witco Chemical Co., Inc.) and 2 g Cab-O-Sil™ (colloidal silicone dioxide, Cabot Corp.), and the mixture was heated to 85° C. in a Slauterback hot melt tank-pump. 3.0 Grams (about 3.3 g) of the wax mixture was delivered to the cup in laminated arrangement to the hydrophilic expansion member.

Beneficial agent formulation: 831 Grams of Multiwax™ X145A and 20 g Cab-O-Sil™ (colloidal silicone dioxide, Cabot Corp.) were melted using a hot plate, and the temperature was adjusted to 80° C. 149 Grams of ivermectin were added, using a high shear mixing apparatus. The temperature was maintained at 68° C. while 8.5 g (about 8.8 mL) aliquots were delivered to individual cup assemblies. The ivermectin formulation was allowed to cool and formed a lamina adjacent to the moveable barrier means.

Density Means: A sintered iron densifier having a 5.1 mm bore axially therethrough was preheated to 60° C., and was inserted into the open end of the cup assembly. The densifier was seated against the beneficial agent formulation lamina. The protruding lip of the cup was heated until softened using a hot air gun, and the lip was crimped over the densifier, forming an exit means.

EXAMPLE 2

Use of Dispensing Device without Loading Dose

A rubber collection vessel was placed over the dispensing device of Example 1, to cover the passageway and collect formulation delivered through the passageway. The devices were either placed in a liquid (in vitro test) or administered to a fistulated cow (in vivo test). Formulation was removed from the collection vessel periodically to determine the release rate. The in vitro and in vivo release rates were comparable and are summarized, with circles, in FIG. 11.

EXAMPLE 3

Prehydration and Use of Dispensing Device without Loading Dose

The dispensing device of Example 1 was placed in 100 mL of water at 40° C. After 21 days, the device was removed from the water and a rubber collection vessel was placed over the device to cover the passageway and collect materials delivered through the passageway. The devices were tested in vitro or in vivo, following the procedures of Example 2, and material was removed from the collection vessel periodically to determine the release rate. The summarized release rates are shown, with squares, in FIG. 11.

EXAMPLE 4

Loading dose

7 Grams ivermectin (Merck) was mixed thoroughly with 13 grams polyethylene oxide (MW 500,000, Union Carbide). 10 mL of anhydrous ethanol was added with further mixing. The wet granulation mix was passed through a 20 mesh screen, allowed to dry overnight, and again passed through a 20 mesh screen. The twice-screened granulation mixture was mixed in a mill with 100 mg magnesium stearate for one minute to produce a tableting mix. 480 Milligrams of the tableting mix was compressed in a 0.9525 cm (⅜-inch) tablet punch.

EXAMPLE 5

Manufacture of Dispensing Device with Loading Dose

The semipermeable wall, expansion means, moveable barrier means, and beneficial agent formulation were produced as shown in Example 1.

Density Means: A sintered iron densifier was produced which has a bore axially therethrough which measures 5.1 mm through most of its length. At 14.8 mm from the outer edge of the bore, the bore widens to 10.2 mm. The densifier was preheated to 60° C. and was inserted into the open end of the cup assembly. The densifier was seated against the beneficial agent formulation lamina. A loading dose according to Example 4 was inserted into the bore of the densifier. The loading dose was covered with a closely fitting perforated plate having a number of perforations. The area of the perforated plate which allows exposure of the loading dose to the environment was 0.095 $cm^2$. The protruding lip of the cup was heated until softened using a hot air gun, and the lip was crimped over the densifier, forming an exit means.

EXAMPLE 6

Use of Dispensing Device with Loading Dose

The dispensing device of Example 5 was placed in an aqueous solution. The drug delivery of the loading dose of the device of Example 5 was determined, in vitro, by measuring, at intervals, the amount of drug in the solution. After depletion of the loading dose, a rubber collection vessel was placed over the device to cover the passageway and collect second beneficial agent formulation delivered through the passageway. The device was replaced into an aqueous solution. Formulation was removed from the collection vessel periodically to determine the release rate. The in vitro release rate is shown, with triangles, in FIG. 11.

Modifications of the above described process and apparatus will be apparent to those skilled in the art. Such modifications are intended to be within the spirit and scope of the following claims.

We claim:

1. A single dispensing device for delivering a beneficial agent to an environment of use over an extended period of time, said dispensing device comprising:
   (a) a first agent delivery means for making a first beneficial agent formulation quickly available to the environment of use, said first agent delivery means comprising:
      (1) a first beneficial agent formulation which comprises at least one beneficial agent, and which releases said beneficial agent within the environment of use substantially throughout the time prior to the release of a second beneficial agent formulation; and
      (2) retaining means for retaining the first beneficial agent formulation in contact with a second agent delivery means while exposing the first beneficial agent formulation and the second agent delivery means to the environment of use; and
   (b) a second agent delivery means for continuous and prolonged delivery of a second beneficial agent formulation to the environment of use, said second agent delivery means comprising:
      (1) a wall that surrounds and defines an internal lumen, the wall comprising a composition that is permeable to the passage of fluid and substantially impermeable to the passage of beneficial agent;
      (2) a second beneficial agent formulation in the lumen that provides a dispensable formulation including at least one beneficial agent to the environment of use;
      (3) an expansion means in the lumen for displacing said second beneficial agent formulation from the interior of the lumen to the environment of use after exposure to the environment of use; and
      (4) an exit means in the dispensing device for delivery of said second beneficial agent formulation to the environment of use.

2. The dispensing device of claim 1 further comprising density means for mounting said device within the rumen of a ruminant animal.

3. The dispensing device of claim 2 wherein the exit means comprises a passageway through said density means.

4. The dispensing device of claim 3 wherein said first beneficial agent formulation is disposed within the exit means.

5. The dispensing device of claim 4 wherein said retaining means comprises a member selected from the group consisting of a perforated plate, a screen, a porous membrane, and a perforated membrane disposed between the environment of use and said first agent formulation.

6. The dispensing device of claim 2 wherein said retaining means comprises a member selected from the group consisting of a perforated plate, a screen, a porous membrane, and a perforated membrane disposed between the environment of use and said first agent formulation.

7. The dispensing device of claim 3 wherein said retaining means comprises a member selected from the group consisting of a perforated plate, a screen, a porous membrane, and a perforated membrane disposed between the environment of use and said first agent formulation.

8. A method of administering to a ruminant a beneficial agent comprising administering orally to the ruminant a device according to claim 4.

9. The dispensing device of claim 1 wherein said first beneficial agent formulation is disposed within the exit means.

10. The dispensing device of claim 9 wherein said retaining means comprises a member selected from the group consisting of a perforated plate, a screen, a porous membrane, and a perforated membrane disposed between the environment of use and said first agent formulation.

11. The dispensing device of claim 1 wherein said retaining means retains said first beneficial agent formulation at or near the surface of the second agent delivery means.

12. The dispensing device of claim 11 wherein said retaining means comprises a member selected from the group consisting of a perforated plate, a screen, a porous membrane, and a perforated membrane disposed between the environment of use and said first agent formulation.

13. The dispensing device of claim 1 wherein said first beneficial agent formulation and said second beneficial agent formulation contain the same beneficial agent.

14. The dispensing device of claim 1 wherein said first beneficial agent formulation is in a tablet form.

15. The dispensing device of claim 1 wherein said beneficial agent is selected from the group consisting of an anthelmintic agent, an antiparasitic agent, an antimicrobial agent, an antibiotic agent, an antibloat agent, an estrus suppression agent, an antiflea agent, a nutrient agent, a hormonal agent, a steroidal agent, and mixtures thereof.

16. The dispensing device of claim 1 wherein said beneficial agent is selected from the group consisting of avermectin, ivermectin, selenium, melengestrol acetate, and mixtures thereof.

17. The dispensing device of claim 1 wherein said retaining means comprises a member selected from the group consisting of a perforated plate, a screen, a porous membrane, and a perforated membrane disposed between the environment of use and said first agent formulation.

18. A method of administering to a ruminant a beneficial agent comprising administering orally to the ruminant a device according to claim 2.

19. A dispensing device for delivering a beneficial agent formulation to an environment of use, said dispensing device comprising:
   (a) a first agent delivery means for making a first beneficial agent formulation available to the environment of use, said first delivery means comprising:
      (1) a first beneficial agent formulation which comprises a beneficial agent, and which releases said beneficial agent over time within the environment of use; and
      (2) retaining means for retaining the first beneficial agent formulation in contact with a second agent delivery means while exposing the first beneficial agent formulation and the second agent delivery means to the environment of use; and
   (b) a second agent delivery means for continuous and prolonged delivery of a second beneficial agent formulation to the environment of use, said second agent delivery means comprising:
      (1) a wall that surrounds and defines an internal lumen, the wall comprising a composition that is permeable to the passage of fluid and substantially impermeable to the passage of beneficial agent;
      (2) a second beneficial agent formulation that contains a different beneficial agent than in the first beneficial agent formulation in the lumen that provides a dispensible formulation comprising a beneficial agent for delivery to the environment of use;
      (3) an expansion means in the lumen for displacing said second beneficial agent formulation from the interior of the lumen to the environment of use after exposure to the environment of use; and 4) an exit means in the dispensing device for delivery of said second beneficial agent formulation to the environment of use.

20. A dispensing device for delivering a beneficial agent to an environment of use, said dispensing device comprising:
   (a) a first agent delivery means for making a first beneficial agent formulation available to the environment of use, said first agent delivery means comprising:
      (1) a first beneficial agent formulation which comprises said beneficial agent, and a hydrophilic polymer and releases said beneficial agent formulation over time within the environment of use; and
      (2) retaining means for retaining the first beneficial agent formulation in contact with a second agent delivery means while exposing the first beneficial agent formulation and the second agent delivery means to the environment of use; and
   (b) a second agent delivery means for continuous and prolonged delivery of a second beneficial agent formulation to the environment of use, said second agent delivery means comprising:
      (1) a wall that surrounds and defines an internal lumen, the wall comprising a composition that is permeable to the passage of fluid and substantially impermeable to the passage of beneficial agent:
      (2) a second beneficial agent formulation in the lumen that provides a dispensable formulation including beneficial agent to the environment of use;
      (3) an expansion means in the lumen for displacing said second beneficial agent formulation from the interior of the lumen to the environment of use after exposure to the environment of use; and
      (4) an exit means in the dispensing device for delivery of said second beneficial agent formulation to the environment of use.

21. A method for administering a beneficial agent to an environment of use for an extended period of time, which method comprises:
   (a) introducing into the environment of use a single delivery device, which device comprises:
      (1) a first agent delivery means for making a first beneficial agent formulation quickly available to the environment of use, said first agent delivery means comprising:
         (i) a first beneficial agent formulation which comprises at least one beneficial agent, and which releases said beneficial agent within the environment of use substantially throughout the time prior to the release of a second beneficial agent formulation; and
         (ii) retaining means for retaining the first beneficial agent formulation in contact with a second agent delivery means while exposing the first beneficial agent formulation and the second agent delivery means to the environment of use; and
      (2) a second agent delivery means for continuous and prolonged delivery of a second beneficial agent formulation to the environment of use, said second agent delivery means comprising:
         (i) a wall that surrounds and defines an internal lumen, the wall comprising a composition that is permeable to the passage of fluid and substantially impermeable to the passage of beneficial agent;
         (ii) a second beneficial agent formulation in the lumen that provides a dispensable formulation including at least one beneficial agent to the environment of use;
         (iii) an expansion means in the lumen for displacing said second beneficial agent formulation from the interior of the lumen to the environment of use after exposure to the environment of use; and
         (iv) an exit means in the dispensing device for delivery of said second beneficial agent formulation to the environment of use;
   (b) releasing agent from said first agent delivery means for an initial portion of said extended period of time; and
   (c) releasing agent from said second agent delivery means for a terminal portion of said extended period of time.

22. A method for administering a beneficial agent to the rumen of ruminant animal for an extended period of time, which method comprises:
   (a) introducing into the rumen of the animal a delivery device, which device comprises:
      (1) a first agent delivery means for making a first beneficial agent formulation quickly available to the rumen of the ruminant, said first agent delivery means comprising:
         (i) a first beneficial agent formulation which comprises at least one beneficial agent, and releases said beneficial agent within the rumen of the ruminant substantially throughout the time prior to the release of a second beneficial agent formulation;
         (ii) retaining means for retaining the first beneficial agent formulation in contact with a second agent delivery means while exposing the first beneficial agent formulation and the second agent delivery means to the rumen of the ruminant; and
      (2) a second agent delivery means for continuous and prolonged delivery of a second beneficial agent formulation to the rumen of the ruminant, said second agent delivery means comprising:
         (i) a wall that surrounds and defines an internal lumen, the wall comprising a composition that is permeable to the passage of fluid and substantially impermeable to the passage of beneficial agent;
         (ii) a second beneficial agent formulation in the lumen that provides a dispensable formulation including at least one beneficial agent to the rumen of the ruminant;
         (iii) an expansion means in the lumen for displacing said second beneficial agent formulation from the interior of the lumen of the rumen of the ruminant;
         (iv) an exit means in the dispensing device for delivery of said second beneficial agent formulation;
   (b) releasing the agent from said first agent delivery device for an initial portion of said extended period of time; and
   (c) releasing the agent from said second agent delivery device for a terminal portion of said extended period of time.

23. A method for administering a beneficial agent to an environment of use for an extended period of time, which method comprises:
   (a) introducing into the environment of use a delivery device, which device comprises:
      (1) a first agent delivery means for making a first beneficial agent formulation quickly available to the environment of use, said first agent delivery means comprising:
         (i) a first beneficial agent formulation which comprises at least one beneficial agent, and releases said beneficial agent within the environment of use substantially throughout the time prior to the release of a second beneficial agent formulation; and (ii) retaining means for retaining the first beneficial agent formulation in contact with a second agent delivery means while exposing the first beneficial agent formulation and the second agent delivery means to the environment of use; and (2) a second agent delivery means for continuous and prolonged delivery of a second beneficial agent formulation to the environment of use, said second agent delivery means comprising:

(i) a wall that surrounds and defines and internal lumen, the wall comprising a composition that is permeable to the passage of fluid and substantially impermeable to the passage of beneficial agent;

(ii) a second beneficial agent formulation in the lumen that provides a dispensable formulation including at least one beneficial agent to the environment of use;

(iii) an expansion means in the lumen for displacing said second beneficial agent formulation from the interior of the lumen to the environment of use after exposure to the environment of use; and (iv) an exit means in the dispensing device for delivery of said beneficial agent formulation to the environment of uses (b) releasing the beneficial agent from said first delivery means for an initial portion of said extended period of time;

(c) releasing agent from said second agent delivery means for a terminal portion of said extended period time; and;

(d) releasing the agent from said first delivery means and said second delivery means at different rates over said extended period of time.

* * * * *